United States Patent [19]

Ogiu

[11] Patent Number: 4,879,991
[45] Date of Patent: Nov. 14, 1989

[54] ENDOSCOPE

[75] Inventor: Hisao Ogiu, Hachioji, Japan

[73] Assignee: Olympus Optical Co., Ltd., Tokyo, Japan

[21] Appl. No.: 119,459

[22] Filed: Nov. 10, 1987

[30] Foreign Application Priority Data

Nov. 12, 1986 [JP] Japan ................................ 61-270365

[51] Int. Cl.[4] .............................................. A61B 1/00
[52] U.S. Cl. .......................................... 128/6; 128/4
[58] Field of Search ...................... 128/6, 4; 350/96.26; 285/381, DIG. 909; 358/98; 356/96.26

[56] References Cited

U.S. PATENT DOCUMENTS

| 3,960,143 | 6/1976 | Terada | 128/4 |
| 4,261,644 | 4/1981 | Giannaris | 350/96.21 |
| 4,290,421 | 9/1981 | Siegmund | 128/6 |
| 4,296,955 | 10/1981 | Martin | 285/381 |
| 4,319,563 | 3/1982 | Kubota | 128/6 |
| 4,558,706 | 12/1985 | Nakada et al. | 128/4 |
| 4,682,585 | 7/1987 | Hilterbrandt | 128/4 |
| 4,706,654 | 11/1987 | Ogiu et al. | 128/4 |
| 4,715,739 | 12/1987 | Rüegg et al. | 285/381 |

FOREIGN PATENT DOCUMENTS

| 0029281 | 5/1981 | European Pat. Off. | 128/6 |
| 3516164 | 11/1985 | Fed. Rep. of Germany | 128/6 |
| 0108459 | 9/1978 | Japan | 350/96.26 |
| 0152728 | 11/1980 | Japan | 128/4 |
| 0020074 | 5/1984 | Japan | 128/4 |
| 61-22566 | of 1986 | Japan . | |

Primary Examiner—Leo P. Picard
Assistant Examiner—Jessica Harrison
Attorney, Agent, or Firm—Armstrong, Nikaido, Marmelstein, Kubovcik & Murray

[57] ABSTRACT

The outer periphery including the peripheral edge of the front end surface of a hard tip member in which an image forming device and illuminating light emitting device are contained and fixed on the tip side of an elongated insertable part is covered with a soft cover member so that the shock of striking the tip part may be absorbed to protect the contents.

16 Claims, 5 Drawing Sheets 4,879,991

ENDOSCOPE

BACKGROUND OF THE INVENTION

1. Field of the Invention and Related Art Statement

This invention relates to an endoscope having a tip covered with a soft material.

Recently, there is extensively used an endoscope whereby an organ or the like within a body cavity can be observed by inserting an elongated insertable part into the body cavity or various curing treatments can be made by using a treating tool inserted through a treating tool channel as required.

Various electronic endoscopes wherein such solid state imaging device as a charge coupled device (CCD) is used for an imaging means have been suggested. Such electronic endoscope has advantages that its resolution is higher than of a fiberscope, it is easy to record and reproduce a picture image and such picture image treatments as the enlargement of a picture image and the comparison of two pictures are easy.

Now, in the above mentioned endoscope, a hard tip part is provided on the tip side of the insertable part. This tip part is provided with a tip body made of a hard member. An objective lens system or the like is contained and fixed in this tip body. A tip part covered with an insulating cover for electric safety is disclosed, for example, in Japanese Patent Publication No. 22566/1986. Such comparatively hard (respectively of Rockwell hardnesses M63, M80, M90 and M90) plastics as polycarbonate, polyacetal, polysulfone and modified PPO (nonyl) or so-called engineering plastics have been used for the above mentioned insulating cover.

However, there are problems that, if the above mentioned tip part is formed of a hard member or is covered with a hard plastic, when this tip part is struck, the shock will be likely to be transmitted to the interior and, by this shock, the cementing part of an objective or the like contained in the above mentioned tip part will be peeled off to leak water or for the visual field, a solid state imaging device or the like in an electronic endoscope will be damaged or a wiring will be cut off.

By the way, an endoscope in which the tip part is covered to the midway with a soft cover member is disclosed in U.S. Pat. No. 4,290,421. However, this cover member does not cover the corner part of the tip surface and therefore has the same defects as of the above described prior art example.

OBJECTS AND SUMMARY OF THE INVENTION

An object of the present invention is to provide an endoscope wherein, even when the tip part is struck, the shock will be reduced to be able to protect the contents.

Another object of the present invention is to provide an endoscope wherein the contents can be effectively protected with a simple formation.

In the present invention, a soft cover member covering the outer periphery of a hard tip part forming member containing an imaging means or the like is provided on the tip side of an insertable part so that, even when the tip part is struck, the shock will be absorbed by this cover member to be able to protect the contents.

BRIEF DESCRIPTION OF THE DRAWINGS

FIG. 1 is a sectioned view of a tip part of an insertable part of an electronic endoscope.

FIG. 2 is a side view showing the entire electronic endoscope.

DETAILED DESCRIPTION OF THE PREFERRED EMBODIMENTS

Figure 2:
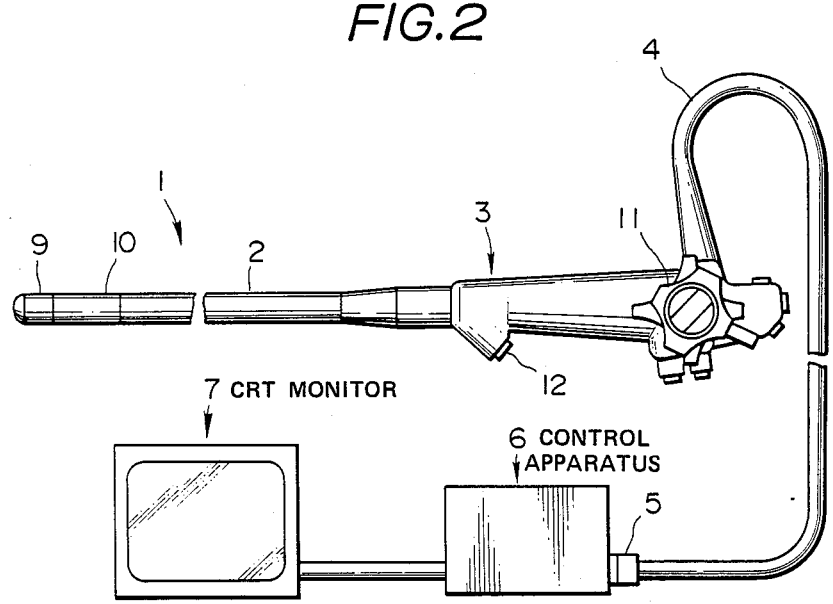

As shown in FIG. 2, in an electronic endoscope 1 of the first embodiment, an operating part 3 of a large diameter is connected to the rear end of an elongated, for example, flexible insertable part 2, a flexible cable 4 is extended sidewise from the rear end part of the above mentioned operating part 3 and a connector 5 is provided at the tip of this cable 4. The above mentioned endoscope 1 is to be connected through the above mentioned connector 5 to a control apparatus 6 containing a light source device and a video signal processing device. Further, a color CRT monitor 7 as a displaying means is to be connected to the above mentioned control apparatus 6.

A hard tip part 9 and a curvable part 10 made by tandem connecting a plurality of articulating frames (not illustrated) on the rear side adjacent to this tip part 9 are provided in turn on the tip side of the above mentioned insertable part 2. The above mentioned curvable part 10 can be curved in the horizontal and vertical directions by rotating a curving operation knob 11 provided on the above mentioned operating part 3. An inserting port 12 communicating with a forceps channel provided within the above mentioned insertable part 2 is provided in the above mentioned operating part 3.

Figure 1:
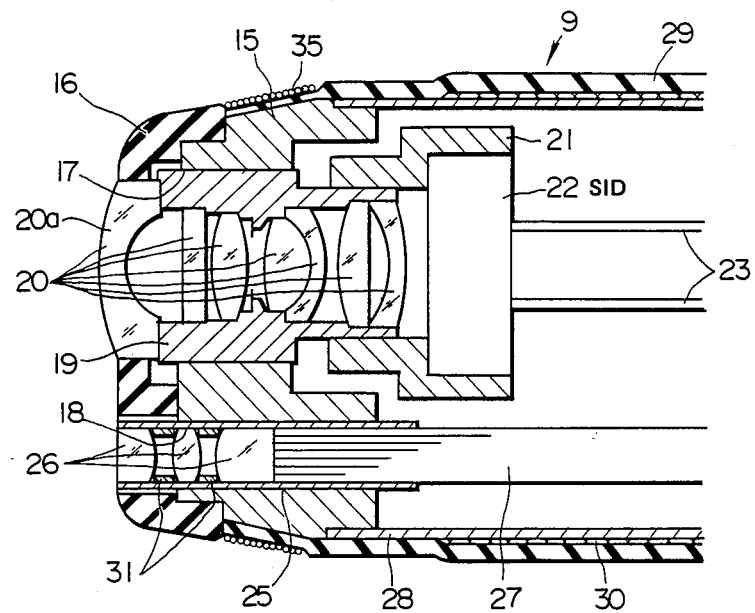
FIGS. 1 and 2 relate to the first embodiment of the present invention.

The above mentioned tip part 9 is formed as shown in FIG. 1.

That is to say, the tip part 9 is provided with a substantially columnar tip body 15 made of such hard member as of a metal. An insulating cover 16 as a cover member is fitted to the tip side of this tip body 15. By the way, the outer peripheral surfaces of the above mentioned tip body 15 and insulating cover 16 are tapered to be smaller on the tip side.

In this embodiment, the above mentioned insulating cover 16 is formed of a soft insulating material. Such soft resin as, for example, polyethylene, urethane or vinyl chloride or such elastomer having an elasticity as synthetic rubber can be used for this soft material. A through hole 17 for containing an observing means and through hole 18 for containing an illuminating means and a through hole for a forceps channel and through hole for an air and water feeding channel not illustrated all passing parallelly in the lengthwise direction of the above mentioned insertable part 2 are formed in the above mentioned tip body 15 and insulating cover 16.

A lens frame 19 is fitted to the above mentioned through hole 17 for containing the observing means. An objective lens system 20 as an image forming optical system is contained, cemented and fixed in this lens frame 19 so that its optical axis may be parallel with the lengthwise direction of the above mentioned insertable part 2. A front objective lens 20a at the foremost end of the above mentioned objective lens system 20 is cemented and fixed to the front end of the above mentioned lens frame 19 or the above mentioned insulating cover 16 or to both of the front end of the lens frame 19 and the insulating cover 16. By the way, the above mentioned front objective lens 20a may be cemented and fixed to the tip body 15.

An element supporting frame 21 is externally fitted and fixed in the tip part to the rear end part of the above mentioned lens frame 19. A solid state imaging device 22 arranged so that the imaging plane may be positioned in the image forming position of the above mentioned objective lens system 20 is held by this element supporting frame 21.

A signal cable 23 connected to the above mentioned solid state imaging device 22 is inserted through the above mentioned insertable part 2 and further through the above mentioned cable 4. The output signal of the above mentioned solid state imaging device 22 is delivered to a video signal processing circuit (not illustrated) within the above mentioned control apparatus 6 through the above mentioned signal cable 23 and the signal cable within the above mentioned cable 4.

On the other hand, a light distributing lens frame 25 is fitted to the above mentioned through hole 18 for containing the illuminating means. A light distributing lens system 26 is fitted to this light distributing lens frame 25 as held at a predetermined spacing by spacers 31. A light guide 27 is connected to the rear end of this light distributing lens system 26, is inserted through the above mentioned insertable part 2 and further through the above mentioned cable 4 and is connected to a light source device (not illustrated) within the above mentioned control apparatus 6 through a light guide within this cable 4.

Figure 3A:
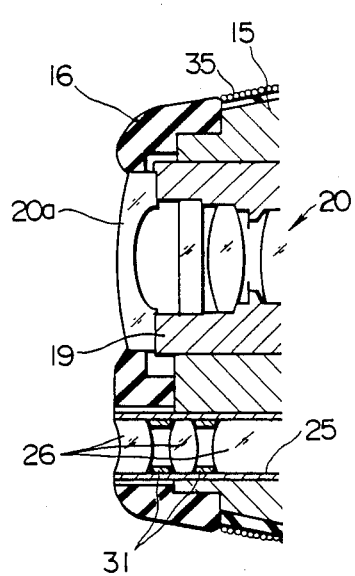
FIGS. 3a and 3b are a sectioned view showing an essential part of a modification of the first embodiment.
Figure 3B:
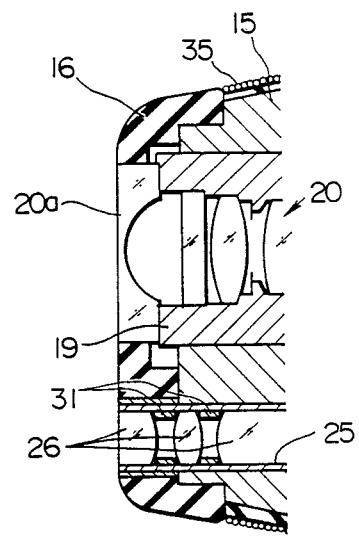

In the illustrated example, the central part of the front end surface of the front objective lens somewhat projects above the outer surface of the front end (front end surface) of the above mentioned insulating cover 16 but the peripheral edge part of the front surface of the above mentioned objective lens system 20 and the outer surface of the light distributing lens system 26 are in substantially the same plane as the outer surface of the front end of the above mentioned insulating cover 16. By the way, in consideration of the protection of the lens, the outer surface of the front ends of the above mentioned objective lens system 20 and light distributing lens system 26 may be inner than the outer surface of the front end of the above mentioned insulating cover 16 as in FIG. 3A. Also, the front end surface of the front objective lens 20a may be in the same place as the front end surface of the insulating cover 16 as in FIG. 3B.

A forceps channel tube not illustrated forming the forceps channel is connected to a through hole for the forceps channel not illustrated, is inserted through the above mentioned insertable part 2 and is connected to the inserting port 12 in the above mentioned operating part 3. An air and water feeding nozzle not illustrated is fitted to the through hole for the air and water feeding channel not illustrated. An air and water feeding tube not illustrated forming the air and water feeding channel is connected to this air and water feeding nozzle, is inserted through the above mentioned insertable part 2 and is connected to an air and water feeding port not illustrated provided in the above mentioned operating part 3.

A tip pipe 28 is externally fitted and fixed to the rear end part of the above mentioned tip body 15. The above mentioned solid state imaging device 22 or the like is contained within this tip pipe 28.

Further, a tube 29 which is an outer cover of the above mentioned insertable part 2 and is made of such flexible insulating material as rubber is connected at the tip to the rear end part of the above mentioned tip body 15. A net tube 30 made by knitting such fine wires as of a metal to be in the form of a net is provided on the inner periphery of this tube 27. The above mentioned signal cable 23 and light guide 27 and the forceps channel and air and water feeding channel not illustrated are inserted through the above mentioned tube 29 and net tube 30.

The above mentioned tube 29 is externally fitted in the tip part to the tapered (conical) outer peripheral part of the above mentioned tip body 15 and is fixed to the above tip body 15 by being cemented with a cementing agent after being wound to be fastened, for example, with a thread-like member 35 in the form of a conical ring. The outer peripheral part of the fixing part of this tube 29 is tapered to be smaller on the tip side in response to the outer peripheral part of the above mentioned tip body 15.

The tapered outer peripheral part of the above mentioned insulating cover 16 and the tapered outer peripheral part of the fixing part of the above mentioned tube 29 are so formed as to continue to be conical.

The above mentioned tip part 9 had better be thin in order to reduce the pain of the patient when it is inserted. However, particularly, in the case of an electronic endoscope, the solid state imaging device 22 is so large that the outside diameter of the tip part 9 corresponding to this solid state imaging device 22 will be large. Therefore, as in this embodiment, the above mentioned tip part 9 is made thin on the tip side and is smoothly tapered on the outer periphery so that the insertion may be easy and the pain of the patient may be reduced. By the way, the outer periphery of the above mentioned insulating cover 16 need not always be tapered.

In the first embodiment and its modification formed as in the above, the insulating cover 16 for the tip part 9 is formed of a soft material so that, for example, in case the tip part 9 is struck against anything during the use, the shock received by the tip part 9 may be absorbed by the soft insulating cover 16 and may be prevented from being transmitted to the interior of the tip part 9, such cemented part as of the objective lens system contained in the tip part 9 may be effectively prevented from peeling off to leak water or fog the visual field, the solid state imaging device or the like may be effectively prevented from being damaged and the cable 23 may be effectively prevented from being broken.

In case the tip part is to be inserted into a body cavity, the tip part 9 will be pushed into the deep part while in contact on the outer peripheral surface with the wall surface within the body cavity but, as the tip part 9 is covered on the outer periphery with the soft cover 16, the wall surface within the body cavity will be able to be effectively prevented from being hurt.

Figure 4:
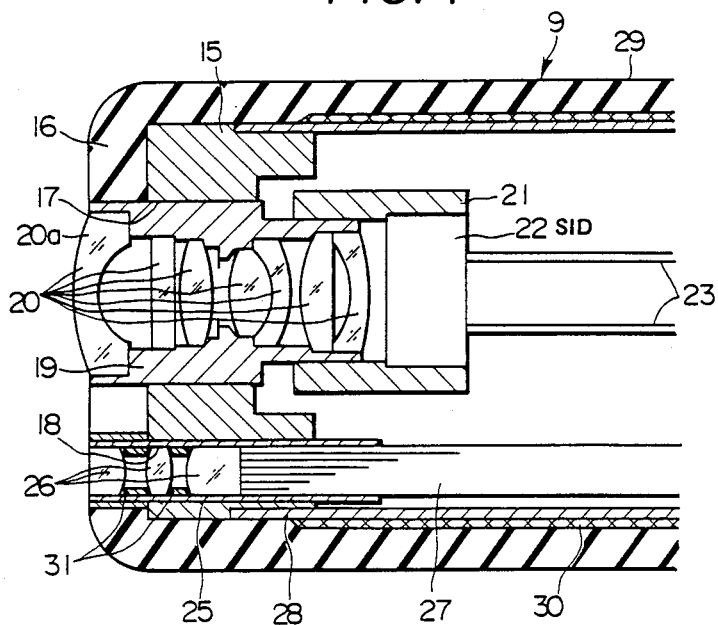
FIG. 4 is a sectioned view of a tip part of an insertable part of an electronic endoscope relating to the second embodiment of the present invention.

FIG. 4 is a sectioned view of an electronic endoscope relating to the second embodiment of the present invention.

In this embodiment, the insulating cover 16 is formed integrally with the tube 29 made of such soft insulating material as rubber. That is to say, the above mentioned tube 29 is closed in the tip part so as to cover the tip body 16 and through holes corresponding respectively to the objective lens system 20 and light distributing system 26 are formed on the tip surface of the tube 29. The tip body 15 is covered with the tip surface of this tube 29 so that the outer surfaces of the above mentioned objective lens system 20 and light distributing lens 26 may be in substantially the same plane as the outer surface of the above mentioned tube 29. By the way, in the illustrated example, the tip part of the tube 29 forming the insulating cover 16 is cemented and fixed to the above mentioned tip body 15 and is not fixed by winding a thread but may be fixed by winding a thread the same as in the first embodiment.

The other formations, operations and effects are the same as in the first embodiment.

Figure 5:
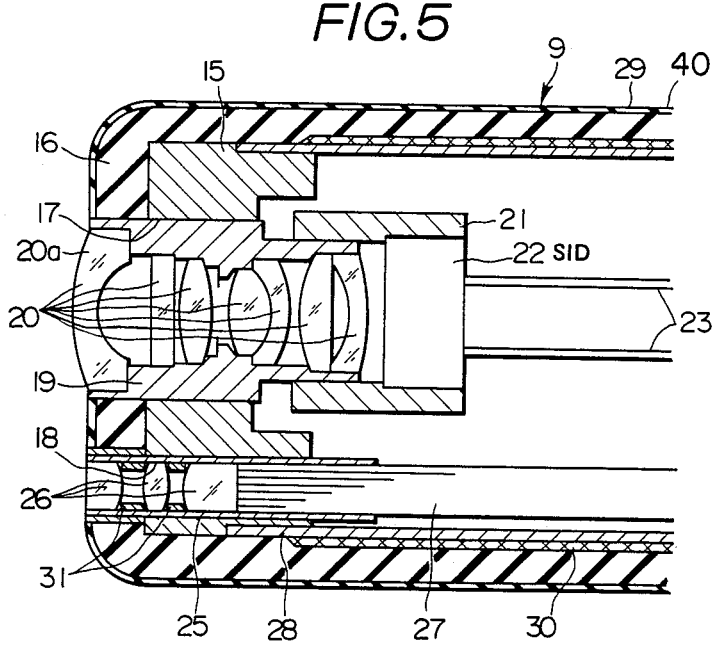
FIG. 5 is a sectioned view showing an essential part of a modification of the second embodiment.
Figure 6:
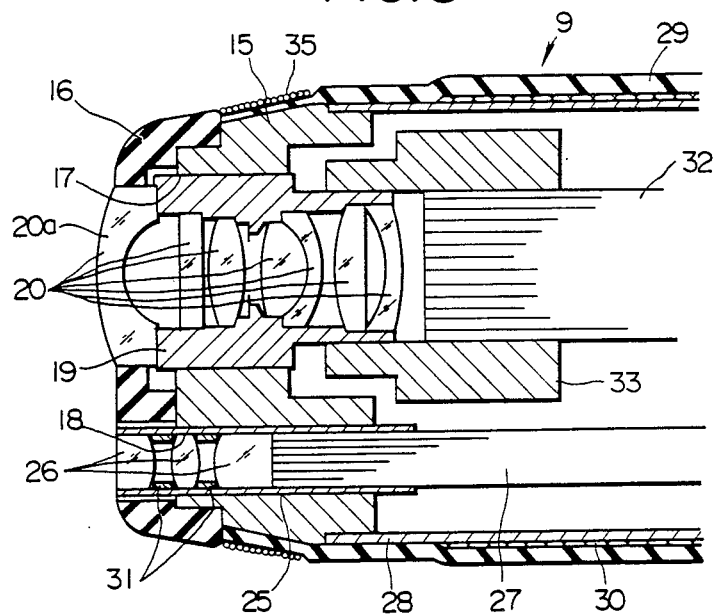
FIG. 6 is a sectioned view of a tip part of a fiberscope of the third embodiment of the present invention.

FIG. 5 shows a modification of the second embodiment. In this modification, a film 40 is provided by coating the outer peripheral surface of the insulating cover 16 in the second embodiment shown in FIG. 4 with such soft material of a small friction coefficient (with a body cavity tissue) as, for example, polytetrafluoroethylene (PTFE).

According to this modification, the tip part can be smoothly inserted into a body cavity and the insulating cover 16 inside the film has a function of absorbing a shock.

By the way, this modification can be applied also to the other embodiments.

By the way, in case it is not necessary to consider the electric insulation, the cover member may be formed of a condustive material.

The present invention can be applied not only to the electronic endoscope but also to an endoscope (fiberscope) wherein an image guide 32 consisting of a flexible fiber bundle is arranged instead of the solid state imaging device 22 in FIG. 1. This image guide 32 is fixed on the tip surface to the lens frame 19 through an image guide fixing frame 33. The incident end surface of this image guide 32 is arranged in the position of the focal plane of the above mentioned objective lens system 20 so that an optical image formed on this incident end surface may be transmitted to an exit end surface on the operating part side and the optical image transmitted from the rear of this exit end surface may be observed.

By the way, the present invention can be applied also to a rigid endoscope in which a relay optical system is used for the image guide.

Figure 7C:
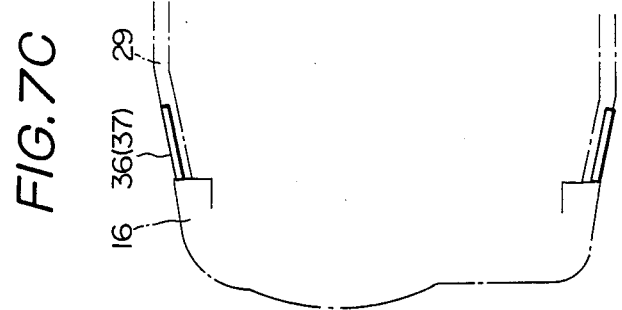
FIGS. 7a and 7b are an explanatory view showing a means for fixing the outer peripheral part of the front end of a tube 29.

By the way, for example, a form memorizing alloy or form memorizing plastic wire 35' may be used instead of the tube fixing means by the thread-like member 35. This wire 35' as wound to be of such inside diameter as is loosely applied as shown in FIG. 7A is applied and is then heated to contract to press and fix the outer peripheral part of the front end of the tube 29 as shown in FIG. 1. This method has an advantage of facilitating the work of fixing the front end of the tube 29.

Figure 7B:
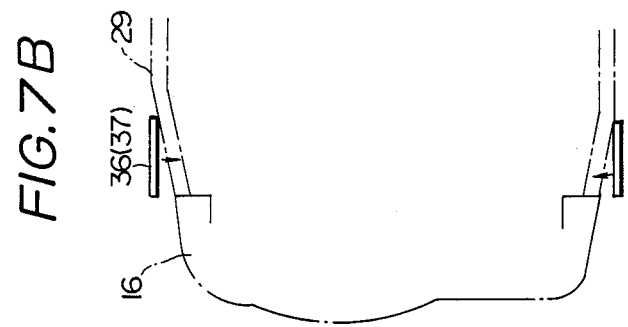
Figure 7A:
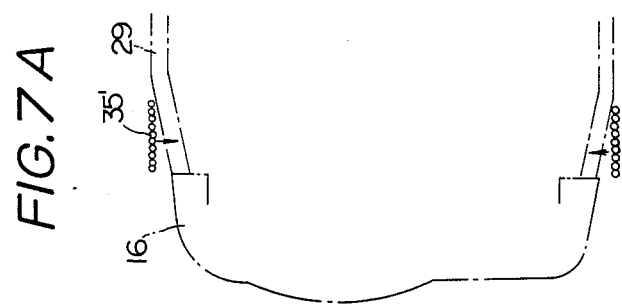

Also, such thermocontracting tube 36 as is shown in FIG. 7B may be used instead of the above mentioned form memorizing member for the thread-like member 35. This thermocontracting tube 36 is applied and is then heated to contract as in FIG. 7C to fix the front end of the tube 29.

Further, a metal pipe 37 may be used instead of the above mentioned thermocontracting tube 36 shown in FIG. 7B. This metal pipe 37 is loosely applied and is then calked on the entire periphery by a calking means to press and fix the tube 29 as in FIG. 7C. Thereby, the work of fixing the tube 29 is made easy.

By the way, the above mentioned metal pipe 37 may be in the form of a C-ring instead of a pipe.

The present invention can be applied not only to a medical endoscope but also to an industrial endoscope.

As explained in the above, according to the present invention, as a cover member made of a soft material to cover the tip body is provided in the tip body, there is an effect that the shock received by the tip part can be prevented from being transmitted to the interior.

In the present invention, it is apparent that working modes different over a wide range can be formed on the basis of the present invention without deviating from the spirit and scope of the invention. The present invention is not restricted by its specific working mode except being limited by the appended claims.

What is claimed is:

1. An endoscope comprising:
   an elongated insertable part having a tip at an insertable front end thereof;
   a hard tip member having apertures for containing and fitting elements at said tip;
   an illuminating means having an illuminating optical system fitted in a first aperture of said hard tip member;
   an observing means having an image forming optical system fitted in a second aperture of said hard tip member; and
   a cover made of a soft elastic flexible material, said cover being disposed around and covering a peripheral edge part of an insertable front end surface of said hard tip member and the front end surface of said hard tip member for protecting said hard tip member from shock while retaining the overall diameter of said insertable front end, said cover having a plurality of apertures aligned with said apertures of said hard tip member.

2. An endoscope according to claim 1 wherein said observing means further includes a solid state imaging device having its imaging plane arranged in the focal plane of said image forming optical system.

3. An endoscope according to claim 1 wherein said observing means further includes an image guide having its incident end surface arranged in the focal plane of said image forming optical system.

4. An endoscope according to any of claims 1 to 3 further including a curvable part attached to a rear end of said hard tip member, said curvable part is covered with a tube and a front end of said tube is fixed to a conical outer surface of said hard tip member.

5. An endoscope according to claim 4 wherein the outer peripheral surface of the front end of said tube covering said curvable part is fixed to said conical outer surface by a ring-like fixing member.

6. An endoscope according to claim 5 wherein said ring-like fixing member is comprised of a length of thread wound in the form of a conical ring on the outer peripheral surface of the front end of said tube covering the conical outer surface of said hard tip member.

7. An endoscope according to claim 5 wherein said ring-like fixing member is comprised of an annulus formed of a thermocontracting form memorizing material.

8. An endoscope according to claim 5 wherein said ring-like fixing member is formed of a tube that contracts when heated.

9. An endoscope according to claim 5 wherein said ring-like fixing member is comprised of a metal ring pressing the outer peripheral surface of the front end of said tube by calking.

10. An endoscope according to claim 1 wherein said cover member is formed of a soft elastic synthetic rubber having an elasticity.

11. An endoscope according to claim 1 wherein said soft cover member is formed of a synthetic resin selected from the group consisting of polyethylene, polyurethane and polyvinyl chloride resins.

12. An endoscope according to claim 1, wherein said cover member for covering said hard tip member is coated with a film having a low coefficient of friction.

13. An endoscope according to claim 12 wherein said film is formed of polytetrafluoroethylene.

14. An endoscope according to claim 1 wherein a front end surface of said image forming optical system is fitted in a position on a rear side of a plane defined by the front end surface of said soft cover member.

15. An endoscope according to claim 1 wherein a front end surface of said image forming optical system is fitted in one of said apertures in said cover member and a peripheral edge of said front end surface is in the same plane as the front end surface of said cover member.

16. An endoscope according to claim 1 wherein said elongated insertable part is covered with a tube made of a soft elastic flexible material and said cover is formed as a portion of said tube.

* * * * *